United States Patent [19]
Speidel

[11] 4,013,265
[45] Mar. 22, 1977

[54] AIR EVACUATION VALVE FOR BLOOD PRESSURE MEASURING DEVICE

[76] Inventor: Blasius Speidel, Hochmeisterstrasse 244, 7455 Jungingen, Germany

[22] Filed: July 30, 1974

[21] Appl. No.: 493,120

[30] Foreign Application Priority Data

July 30, 1973 Germany .......................... 2338596
June 18, 1974 Germany .......................... 2429046

[52] U.S. Cl. .......................... 251/205; 128/2.05 G; 251/263
[51] Int. Cl.² .......................................... F16K 24/00
[58] Field of Search ............... 128/2.05 G, 2.05 M, 128/2.05 A, 2.05 C, 274; 137/625.3, 625.33; 251/205, 263

[56] References Cited
UNITED STATES PATENTS

| | | | |
|---|---|---|---|
| 2,006,878 | 7/1935 | Bandoly | 128/2.05 G X |
| 3,187,775 | 6/1965 | Pinnell | 137/625.3 |
| 3,254,671 | 6/1966 | Berliner | 128/2.05 G X |
| 3,626,959 | 12/1971 | Santomieri | 128/274 X |
| 3,707,972 | 1/1973 | Villari et al. | 128/274 X |
| 3,738,357 | 6/1973 | Hayes | 128/2.05 G |
| 3,779,236 | 12/1973 | Stewart | 128/2.05 G |

FOREIGN PATENTS OR APPLICATIONS 2,118,295 10/1972 Germany .......................... 128/205 G

*Primary Examiner*—Kyle L. Howell
*Attorney, Agent, or Firm*—Joseph A. Geiger

[57] ABSTRACT

A blood pressure measuring device with a quick-evacuation air valve, where the cone-shaped valve plunger has a bypass channel reaching from the pressureless side to a point on the sealing surface of the plunger which, at the maximum normal opening stroke of the latter remains within the throttling range of the valve, but which after an additional opening motion against an abruptly higher spring bias, is opened to the pressure side, thereby rapidly evacuating the device. A detent serves to hold the actuating lever of the valve in its quick-evacuation position.

16 Claims, 10 Drawing Figures

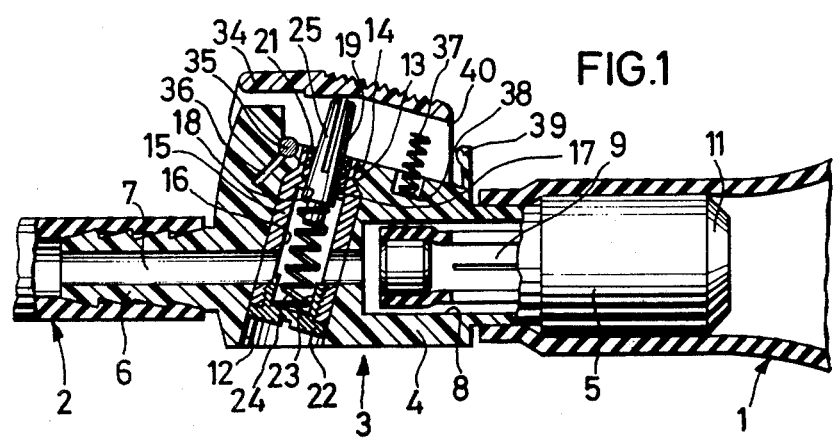
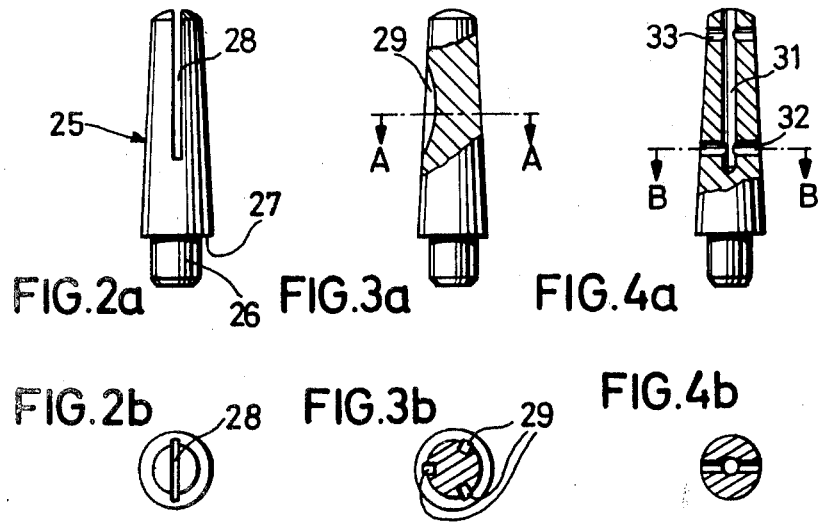

AIR EVACUATION VALVE FOR BLOOD PRESSURE MEASURING DEVICE

BACKGROUND OF THE INVENTION

1. Field of the Invention

The present invention relates to blood pressure measuring devices of the type having an inflatable measuring sleeve, and in particular to blood pressure measuring devices which are equipped with a manually operable valve for the evacuation of the air from the measuring sleeve.

2. Description of the Prior Art

Blood pressure measuring devices of the type mentioned above are known from the prior art. One such device is described in the Offenlegungsschrift (German Printed Application) No. 2,118,295. This device features an air evacuation valve which is operable under finger pressure, using a thumb, for example, thereby making it possible to operate both manual pump and the evacuation valve with one hand only. This arrangement permits a convenient and sensitive control of the measuring device, so that the pressure inside the measuring sleeve can be lowered at the exact desired speed. With this instrument, it is no longer necessary to remove the pump and to place it aside. Rather, the pump itself will serve as a convenient handle for the compact valve housing mounted adjacent thereto.

The standard blood pressure test consists of measuring the systolic and diastolic pressures, the procedure being normally terminated as soon as the diastolic pressure has been ascertained. At this point, the measuring sleeve is still subjected to a considerable amount of pressure, which has to be lowered to zero, before the measuring sleeve is free of pressure and tension for removal from the limb on which the blood pressure test has been performed. This elimination of the residual air pressure from the measuring sleeve makes it necessary to maintain the spring-loaded plunger of the evacuation valve open, until such time as all the air is escaped from the measuring sleeve. However, because the pressure decrease follows an exponential function, the escape of air consumes a comparatively great amount of time, especially in the lower pressure range. With the intent of relieving the technician operating the blood pressure measuring device, it has been suggested, in a proposed solution which is not part of the prior art, to provide a locking means in conjunction with the actuating member of the valve plunger so as to maintain the latter in its open position, until the locking means is released. This solution does relieve the operating technician who, during this time, could for instance record the measured blood pressure values. However, the patient on which the blood pressure test has been performed must wait all this time with the measuring sleeve still attached, until the latter is completely free of pressure, before it can be removed from his limb.

SUMMARY OF THE INVENTION

Underlying the present invention is the objective of improving the earlier-mentioned blood pressure measuring device in such a way that, following termination of the measurements, the residual pressure contained in the measuring sleeve can be removed as rapidly as possible.

According to the present invention, this objective is attained by providing the valve plunger with a bypass channel leading to the seating surface of the valve from the pressurefree side of the valve plunger and extending in the direction of the pressure side of the valve plunger to a point along the seating surface which, under normal opening actuation of the valve plunger, remains within the throttling effect of the valve seat.

This novel design of the valve plunger makes it possible to reduce the pressure during the measuring procedure with the necessary sensitivity as was the case in the past, by operating the valve within its normal opening stroke, and to very quickly evacuate the residual pressure from the measuring sleeve, by moving the valve plunger beyond its normal operating stroke, so that the bypass channel is added to the normal throttling action of the valve, thereby greatly increasing the flow cross section through the valve.

It should be understood, of course, that this novel blood pressure measuring device may also be provided with the earlier-mentioned locking means for the operation of the evacuation valve. The technician then no longer needs to hold the blood pressure measuring device in his hand, not even for the short period of time now necessary for reducing the pressure inside the measuring sleeve to zero. She can now release the pump and the attached evacuation valve from her hand, immediately after opening of the bypass channel, and devote her attention to the person tested, removing from his limb the measuring sleeve, which, after this short moment has become completely pressureless.

BRIEF DESCRIPTION OF THE DRAWINGS

Further special features and advantages of the invention will become apparent from the description following below, when taken together with the accompanying drawings which illustrate, by way of example, several embodiments of the invention, represented in the various figures as follows:

FIG. 1 shows portions of a blood pressure measuring device embodying the invention, the air evacuation valve being shown in a longitudinal cross section;

FIGS. 2a and 2b show, in an enlarged elevation and plan view, respectively, the valve plunger of the air valve of FIG. 1;

FIGS. 3a and 3b show, in similar enlarged views, a modified valve plunger, FIG. 3b being a cross section taken along line A—A of FIG. 3a;

FIGS. 4a and 4b show, again in enlarged views, a third version of the valve plunger of the invention, FIG. 4b being a cross section along line B—B of FIG. 4a;

DESCRIPTION OF THE PREFERRED EMBODIMENTS

Figure 5:
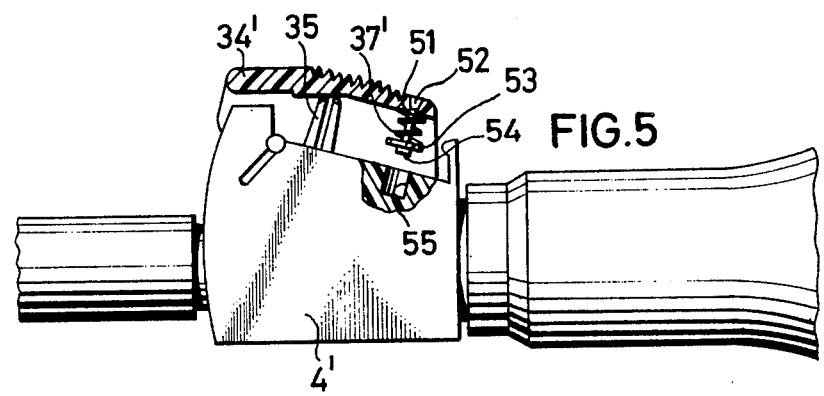
FIG. 5 is similar to FIG. 1, showing a modified actuating handle of the air valve in cross section.

In FIG. 1 of the drawing is illustrated a blood pressure measuring device, the measuring sleeve and the pressure gauge being not shown. Of the rubber bulb 1 and of the pressure line 2 which leads to the measuring sleeve and pressure gauge, only the connecting portions are shown.

The evacuation valve 3 of the device has a valve housing 4, injection molded of plastic material, with a gererally blockshaped outling. On its two lonitudinal ends are arranged connecting nipples, the right-hand connecting nipple 5 of FIG. 1 carrying the hose-shaped end portion of the rubber bulb 1, while the left-hand connecting nipple 6 carries the end portion of the pressure line 2 which connects the evacuation valve 3 and the rubber bulb 1 to the blood pressure measuring sleeve and to the associated pressure gauge, not shown in the drawing.

The valve housing 4 is traversed by a longitudinal bore 7 reaching through the connecting nipples 5 and 6, thereby establishing a straight connection between the rubber bulb 1 of the pump and the pressure line 2. The right-hand portion of bore 7, located inside the connecting nipple 5 for the rubber bulb 1, has an enlarged bore portion 8, inside which is accommodated a check valve 9. The latter is held in place by means of a threaded plug 11 with a central throughbore, the plug 11 being screwed onto a suitable thread on the end portion of the connecting nipple. In the non-enlarged portion of the longitudinal bore 7 inside the valve housing 4 is arranged a cross bore 12, the axis of which intersects the longitudinal bore 7 at an angle of approximately 75 degrees. The cross bore 12 is a throughbore, narrowed on one end by an inwardly projecting tapered shoulder 13 to define a short bore portion 14 of smaller diameter. Inside the cross bore 12 is arranged a metallic valve insert 15 extending over a major portion of the length of the cross bore 12 of valve housing 4. In the area of the reduced-diameter bore portion 14, the valve insert 15 is correspondingly reduced in diameter. The valve insert 15 has a center bore 16 serving as an evacuation channel for the evacuation valve 3, the bore 16 being reduced to a shoulder bore 18, by means of a cylindrical shoulder 17, on that end of the valve insert which is reduced in diameter. This bore portion of the valve insert has a cylindrical recess 19 reaching from the end of the insert to the vicinity of shoulder 17, a valve seat ring 21 of plastic material being firmly fitted in the recess 19. This ring has a tapered bore with a doubletaper angle of approximately 6 degrees serving as a valve seat. The center bore 16 further has a female thread on its end opposite the shoulder bore 18, an end cap 22 being tightly screwed into the thread. This end cap has on its inner side an axially oriented cylindrical recess 23 into which is fitted one end of a helical compression spring 24 serving as a valve closing spring. The opposite end of the closing spring 24 engages a valve plunger 25 which reaches axially through the valve seat ring 21 and which engages its seating portion under the action of the closing spring 24.

The valve plunger 25 has the shape of an elongated narrow cone. On its extremity of larger diameter it has a cylindrical extension 26 of slightly smaller diameter, thereby defining a ring shoulder 27 on that end of the valve plunger 25. The cylindrical extension 26 serves as a guide, and the shoulder 27 as an abutment face for the second end of the closing spring 24.

The tapered valve plunger 25 includes a bypass channel leading to its sealing surface, the bypass channel extending from that extremity of the valve plunger which is located outside the valve seat ring 21, beyond the valve insert 15, in the direction towards the pressurized side at the inside of the valve insert 15, to a point on the sealing surface which, under the normal opening stroke of the valve plunger 25, remains within the range of the throttling action of the valve seat of ring 21. Because of this arrangement of the bypass channel, the latter remains practically without effect, as long as the valve plunger 25 is opened within its normal opening stroke, so that, during a measurement for the determination of the blood pressure values, the pressurized air contained inside the measuring sleeve and inside the longitudinal bore 7 and the center bore 16 can escape only through the throttling cross section which is defined between the valve seat of the valve seat ring 21 and the valve plunger 25 which is lifted from said seat in a sensitively adjustable motion. However, if the valve plunger 25 is forcibly moved beyond its normal fully open position, against the bias of the closing spring 24, towards the inside of the valve insert 15 so that it is further lifted from the valve seat ring 21, then the pressure-side end of the bypass channel moves outside of the throttling range of the valve seat, thereby adding its cross section to the normally available throttling cross section of the valve, with the effect that the total flow cross section is greatly increased. From this it follows that the pressurized air contained inside the measuring sleeve and inside the pressure line 2 very quickly flows out through the evacuation valve 3. FIGS. 2 through 4 illustrate three different versions of the bypass channel, which will be described in more detail in the following:

In the first embodiment, illustrated in FIGS. 2a and 2b, the bypass channel is formed by a slit 28, arranged in the axial plane of the valve plunger 25.

In the second embodiment, according to FIGS. 3a and 3b, the bypass channel takes the form of three radial recesses 29 which are arranged at regular angular intervals on the circumference of the cone and which may be milled or ground into the sealing surface of the valve plunger 25. In the third embodiment, according to FIGS. 4a and 4b, the bypass channel is formed by an axially extending blind bore 31 and a communicating transverse throughbore 32. Near the smaller extremity of the valve plunger 25, which always remains outside the valve insert 15 and thus in the pressureless space, is further arranged a second transverse throughbore 33 also communicating with the axial blind bore 31. This second transverse bore opens the axial blind bore 31 into the pressureless space even then, when the valve plunger 25 is operated through a force acting against its rounded end face at the smaller cone diameter, the force being exerted either directly by a finger, or transmitted through the intermediate of an actuating member, whereby the plunger 25 is disengaged from its valve seat.

Although it is possible to operate the valve plunger 25 by direct finger pressure, by engaging its extremity which protrudes from the valve insert 15, its actuation is facilitated through the arrangement of an actuating lever 34 which is so mounted on the valve housing 4 that that portion of the valve plunger 25 which protrudes from the valve insert 15 is positioned in the path of this actuating lever. The latter is a rocking lever being pivotable around a pivot pin 35 retained in the valve housing 4 and extending at a right angle to its longitudinal bore 7. The actuating lever is generally U-shaped. The opening between its two lateral leg portions in at least equal to the width of the valve housing 4, as measured in the plane which is perpendicular to the plane of the drawing. The pivot axis is positioned at a certain distance from the bridge portion of the actuating lever, thereby also acting as a connecting member between the two leg portions. The pivot pin 35 is positioned in a split bearing defined by a recess in the valve housing 4, the slit 36 thus forming opposite bearing sections for the pivot pin 35. This slit provides a certain resiliency for the two bearing sections so that, when the rocking lever is mounted, its pivot pin 35 can be forcibly engaged between the bearing sections in a snapping action. Because the pivot pin 35 is arranged near one extremity of the rocking lever 34, and the longitudinal axis of the valve plunger 25 is located at a distance from this pivot pin 35 and extends transversely to the bridge portion of the rocking lever, the outer surface of which is serrated and extends beyond the intersection point with the axis of the valve plunger 25, the actuation of the latter is not only facilitated through the availability of a large pressure surface, but an additional leverage is provided between the movements of the actuating lever 34 and the valve plunger 25. The operational sensitivity of the actuation of the valve plunger 25 is thereby further increased.

On the narrow face of the valve housing 4 which is covered by the actuating lever 34, there is further arranged, in the path of the bridge portion of the actuating lever 34, an additional counter spring 37 in the form of a helical compression spring. This spring is seated inside a blind bore 38, arranged approximately parallel to the cross bore 12, the counter spring 37 having an enlarged last coil retaining it against the bottom of the bore 38. The length of the counter spring 37 and the depth of the blind bore 38 are so coordinated that the bridge portion of the actuating lever 34 touches the free end of the counter spring 37 at that point of its displacement stroke at which the valve plunger 25, which is engaged by the actuating lever 34, defines its maximum normal opening stroke. Beyond this point of the actuating stroke of lever 34, the necessary actuating force is greatly increased so that the person operating the apparatus senses a transition from the normal opening stroke to the evacuation stroke. This transition can be made still more evident, if the counter spring 37 is preloaded, even before the actuating lever comes in contact with it, so that the necessary actuating force at this point of the actuating stroke is abruptly increased, as is the case in the modified embodiment illustrated in FIG. 5. Here, the counter spring 37' is retained by a pin 51 which is anchored in the bridge portion of the actuating lever 34' and which extends inwardly from the latter approximately perpendicularly thereto between the two lateral leg portions of the actuating lever. This pin 51 has on one extremity a head 52, resembling, for example, the head of a flat head rivet, the large diameter of the taper being at the outer end of pin 51. This head 52 retains the pin 51 inside a suitable bore in the bridge portion of the actuating lever 34'. In addition to holding the counter spring 37', the pin 55 also accommodates a washer 53, the bore of which is slightly larger than the pin diameter, thereby permitting the washer to slide along the pin, the outer diameter of the washer corresponding to the outer diameter of the counter spring 37' so as to define a spring rest for the latter. The counter spring 37' and the washer 53 are retained on the pin 51 by means of a second head 54 on the free end of pin 51. This second head 54 is formed only after insertion of the counter spring 37' and washer 53 over pin 51, by swaging or flattening the pin end portion, for example. The distance between the second head 54 and the underside of the bridge portion of the actuating lever 34' is so coordinated with the free length of the counter spring 37', plus the thickness of washer 53, that the counter spring 37' is compressed a certain distance prior to the forming of head 54 so that the spring bears with the desired preload against the washer 53. Along the path of the free end of pin 51, with its head 52, is arranged in the valve housing 4' a suitable recess 55 whose diameter and depth are such that the head 54 can penetrate into it, while the washer 53 abuts against the edge surrounding the recess 55. The distance between the washer 53 and the edge of the recess 55 is preferably such that the contact between the washer 53 and the valve housing is established at that point at which the actuating lever 34' and the valve plunger 25 have executed their maximum normal opening stroke so that the transition to the now following quick evacuation stroke is very distinctly felt by the operator as a sharp increase in the force needed for actuating the lever 34'.

In order to further improve the operation of the blood pressure measuring device with its quick evacuation feature at the end of a measurement, the valve housing 4 further includes a detent member 39 which reaches a small distance into the path of the rear edge 40 of the rocking lever 34, at a point along said path at which the rocking lever has moved the valve plunger 25 beyond its normal opening position and into the valve insert 15 for quick evacuation of the air. The detent member 39 is preferably in the form of a rounded protrusion arranged at the end of a tongue-shaped extension which is oriented approximately parallel to the motion path of edge 40 of the rocking lever. The latter thus displaces the detent member 39 as it moves past it, whereupon the member 39 springs back, thereby retaining the rocking lever 34 in its pivoted position, until it is released by a force applied to its outer surface at a point forward of the pivot pin 35.

Figure 6:
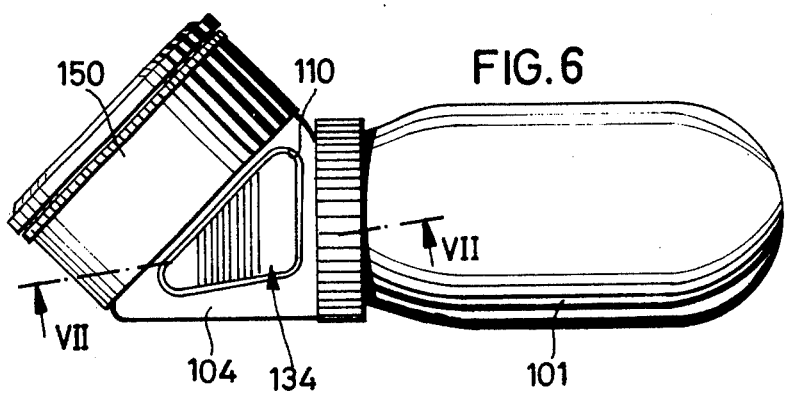
FIG. 6 illustrates, in an elevational view, a different overall arrangement of a blood pressure measuring device incorporating the present invention.
Figure 7:
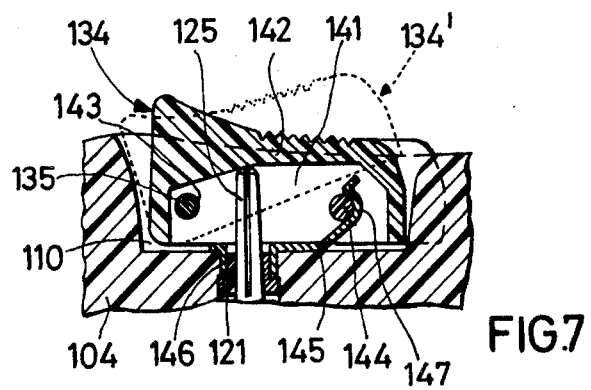
FIG. 7 is an enlarged cross-sectional detail of the device of FIG. 6, sectioned along line VII—VII thereof.

In the embodiment illustrated in FIGS. 6 and 7, the blood pressure measuring device has a modified valve housing which, in addition to the connecting nipples for the rubber valve of the pump and for the pressure line, further includes directly mounted thereon a pressure gauge 150. In the following description relating to this second embodiment reference will be made to parts which are identical or similar to the earlier-described elements of the first embodiment of the invention; the corresponding reference numerals used, therefore, will have an additional 100-digit, thereby showing the relationship between the parts in the context of the first embodiment.

The valve housing 104, in this case, has the approximate shape of an obliquely cut cylinder, with an end face perpendicular to the cylinder axis to which the rubber bulb 101 of the pump is connected, and an obliquely oriented end face on which the pressure gauge 150 is mounted. The actuating lever 134 is adapted in its shape to this particular shape of the valve housing, having a generally triangular outline, as can be seen in the view of FIG. 6, the lever being further partially received within a recess 110 of the valve housing 104, a portion of the lever protruding from the recess in its normal position, as indicated by dotted lines and reference numeral 134' in FIG. 7. The actuating lever 134 has on its side opposite its serrated outer surface a cavity 141 surrounded on all sides by a wall. Into this cavity extends that portion of the valve plunger 125 which protrudes from the valve seat ring 121, contacting the inside surface of the upper wall 142 above the cavity 141. In the normal lever position 134', in which the actuating lever 134 is shown in dotted lines, when the inner side of the lever wall 142 rests against the closed valve plunger 125, which then extends farthest from the valve housing 104, it will be necessary that the outer contour of the actuating lever position 134', shown on the left-hand side in FIG. 7, has sufficient clearance to the adjacent wall of the housing recess 110 so that the valve plunger 125 can safely occupy its closed position, considering manufacturing tolerances.

The pivot support for the actuating lever 134 may be the same as in the first embodiment, except for the modification that, in this case, because of the comparatively stiff design of the valve housing, the latter is not slit for the snap insertion of the pivot pin, but the opposing bearing sections are provided on the actuating lever itself, each of the lateral walls surrounding the cavity 141 of the lever having a slit defining said resilient bearing sections. However, because of the enclosed design of the actuating lever, a comparatively resilient material is preferred, so that the two bearing sections can be spread apart sufficiently so as to receive and safely retain the pivot pin. If the actuating lever 134 is made of a comparatively non-resilient material, in order to increase its resistance against deformation, it is reccommended that the pivot pin 135 be provided as shown in FIG. 7 as a threaded pin which is inserted into an outwardly open bore in the valve housing 104 and screwed tightly into the latter, the pin 135 reaching through appropriate bores 143 in the lateral walls of the actuating lever 134.

The detent means connected with the actuating lever 134 of FIG. 7, means of which the actuating lever can be retained in the position shown in full lines, is designed in this case as a round part, for example, a pin 144, extending through the lever cavity 141 between appropriate bores in its lateral walls, or it may be an integral portion of the actuating lever itself, if the latter is an injection-molded part. The cooperating member of the valve housing 104, defining the other part of the detent means, is a spring 145 having the shape of a leaf spring which is being bent by the pin 144. One extremity of the spring 145 is attached at the bottom of the housing recess 110, in the area of the valve seat ring 121, having an anchoring sleeve 146 either extending integrally therefrom, or attached thereto, and reaching into the cross bore or the valve housing 104 so as to enclose the valve seat ring 121. The other end of the spring 145 is bent upwardly away from the bottom of recess 110, having an S-shaped outline, so as to reach into the movement path of the pin 144, thereby defining a resiliently yielding detent notch 147 engaging pin 144. When the actuating lever 134 is depressed until it reaches the position shown in full lines, its pin 144 thus engages the notch 147, the lever being releasable through a force exerted against the raised lever surface beyond the pivot pin 135. Instead of having a pin 144, the actuating lever 134 may also be provided with a suitable bracket-shaped extension on the inside of the right-hand lateral wall enclosing the cavity 141 (FIG. 7), the free end of the spring being then engaged on that side of its S-shape which is opposite from that shown in the drawing.

I Claim:
1. An air evacuation valve for the adjustable slow release of air from a pressurized air system and for the selective quick deflation of said system, which is particularly suited for use in conjunction with a blood pressure measuring device, for example, the valve comprising in combination:

a valve housing having a main bore communicating with said pressurized air system;

a cross bore in said housing extending outwardly from the housing main bore to an outlet to the atmosphere, said cross bore having a bore portion defining a valve seat separating the inside of the housing from said outlet;

a valve plunger received inside the cross bore so as to be axially movable therealong, the valve plunger having a first length portion located axially inside the valve seat and a second length portion extending through the valve seat to the outside of the housing, the second plunger length portion cooperating with the valve seat so as to progressively open an air throttling passage between it and the valve seat, in response to a displacement of the valve plunger towards the inside of the housing within the range of a predetermined axial opening stroke;

means for biasing the valve plunger axially outwardly in opposition to its opening displacement, so as to close said air throttling passage;

a bypass channel arranged in the second length portion of the valve plunger and extending from a portion thereof which is always exposed to the atmosphere to a point on the valve plunger which, when the latter has reached the inner end of its normal opening strokes, is positioned within the range of said throttling passage between said second plunger length portion and the valve seat, and which, when the valve plunger is forcibly moved inwardly beyond said end point, connects the inside of the housing with the atmosphere independently of the throttling passage, thereby permitting a quick bypass evacuation of air from the pressurized air system.

2. An air evacuation valve as defined in Claim 1, wherein:

the second length portion of the valve plunger has the shape of an outwardly narrowing slim cone;

the valve seat has a matching taper cooperating with the conical length portion of the plunger;

the bypass channel in the valve plunger has an inlet end which, when the valve plunger is positioned at the inner end point of its normal opening stroke, is located in approximate alignment with the inner edge of the valve seat past which the pressurized air enters the throttling passage of the valve.

3. An air evacuation valve as defined in claim 2, wherein the bypass channel of the valve plunger has the form of a central longitudinal slot extending from the outer extremity of the valve plunger to the channel inlet.

4. An air evacuation valve as defined in claim 2, wherein the bypass channel of the valve plunger has the form of a longitudinal groove in the conical length portion of the plunger.

5. An air evacuation valve as defined in claim 4, wherein the bypass channel is constituted by a plurality of angularly regularly spaced longitudinal grooves.

6. An air evacuation valve as defined in claim 2, wherein the bypass channel includes a blind center bore in the second length portion of the valve plunger and a channel inlet in the form of a transvers bore communicating with the blind end portion of the said center bore.

7. An air evacuation valve as defined in claim 6, wherein
the bypass channel further includes a second transverse bore communicating with said center bore so as to form a channel outlet at a point on the valve plunger which always remains outside the range of the valve seat.

8. An air evacuation valve as defined in claim 1, further comprising:
secondary spring means for abruptly increasing the bias against the opening motion of the valve plunger as soon as the latter moves beyond said end point of its normal opening stroke.

9. An evacuation valve as defined in claim 1, further comprising:
an actuating lever movably connected to the valve housing and engaging the valve plunger on the extremity of its second length portion so as to move it axially along said opening stroke and said distance beyond the end point of its normal opening stroke; and
secondary spring means for abruptly exerting a bias against said opening motion of the actuating lever, as soon as the latter moves the valve plunger beyond said end point of its normal opening stroke.

10. An air evacuation valve as defined in claim 9, wherein
the secondary spring means includes a spring arranged between the actuating lever and the valve housing, said spring being deflected when the actuating lever moves the valve plunger beyond its opening stroke end point.

11. An air evacuation valve as defined in claim 9, wherein
the secondary spring means includes a compression spring arranged between the actuating lever and the valve housing, and a pin retaining the spring against one of said two parts in an axially preloaded condition, the spring being further compressed when the actuating lever moves the valve plunger beyond its opening stroke end point.

12. An air evacuation valve as defined in claim 9, further comprising
means for releasably retaining the actuating lever in a position in which said lever holds the valve plunger open for bypass evacuation.

13. An air evacuation valve as defined in claim 12, wherein:
the actuating lever is a rocking lever pivotably connected to the valve housing; and
the retaining means includes a resilient detent extension and a cooperating detent member, one being defined by the valve housing and the other being defined by the rocking lever; the detent extension and the detent member cooperating in a snap action so that the retaining means can be engaged and released by forcibly pivoting the rocking lever into and out of said position.

14. An air evacuation valve as defined in claim 13, wherein:
the resilient detent extension of the retaining means extends from the valve housing in a direction approximately tangential to the pivot motion of the rocking lever, said extension having a retaining nose at its far extremity; and
the cooperating detent member is an edge portion of the rocking lever engaging the protrusion of the detent extension.

15. An air evacuation valve as defined in claim 14, wherein:
the resilient detent extension is a leaf spring attached on one end to the valve housing and having a notch formation at its free end; and
the detent member is a rounded part of the rocking lever cooperating with the notch formation of the leaf spring.

16. An air evacuation valve as defined in claim 15, wherein
the rocking lever has a cross-sectionally U-shaped profile, the rounded part being a pin-shaped member extending between the leg portions of said profile substantially in parallel alignment with the pivot axis of the rocking lever.

* * * * *